United States Patent [19]

Basile et al.

[11] Patent Number: 5,413,563
[45] Date of Patent: May 9, 1995

[54] PRE-FILLED SYRINGE HAVING A PLUNGER, PLUNGER INSERT AND PLUNGER ROD

[75] Inventors: Peter A. Basile, Lawrenceville; Scott C. Brown, Princeton; Fred E. Snyder, Princeton Junction, all of N.J.; Joseph V. Tirrell, Birdsboro, Pa.

[73] Assignee: Sterling Winthrop Inc., New York, N.Y.

[21] Appl. No.: 239,087

[22] Filed: May 6, 1994

[51] Int. Cl.6 .............................................. A61M 5/00
[52] U.S. Cl. ................................. 604/218; 604/228; 604/230
[58] Field of Search ............... 604/218, 220, 221, 222, 604/228, 230, 232, 187, 110

[56] References Cited

U.S. PATENT DOCUMENTS

| | | |
|---|---|---|
| Re. 32,974 | 7/1989 | Porat et al. . |
| 1,222,424 | 4/1917 | Laurent . |
| 1,707,880 | 4/1929 | Sheets . |
| 3,669,111 | 6/1972 | Dubner . |
| 3,705,582 | 12/1972 | Stumpf et al. . |
| 3,766,918 | 10/1973 | Kessel . |
| 3,834,387 | 9/1974 | Brown . |
| 4,216,771 | 8/1980 | Arlers et al. . |
| 4,299,238 | 11/1981 | Baidwan et al. . |
| 4,333,457 | 6/1982 | Margulies . |
| 4,931,043 | 6/1990 | Ray et al. ...................... 604/218 X |
| 5,009,646 | 4/1991 | Sudo et al. .................... 604/230 |
| 5,032,114 | 7/1991 | Olouson ...................... 604/228 X |
| 5,147,328 | 9/1992 | Dragosits et al. ................... 604/218 |

*Primary Examiner*—John D. Yasko
*Attorney, Agent, or Firm*—Fish & Richardson

[57] ABSTRACT

Disclosed are pre-filled syringes equipped with an improved plunger having a plunge insert and a plunger rod, characterized by a leak-proof seal and easy sliding property.

18 Claims, 3 Drawing Sheets

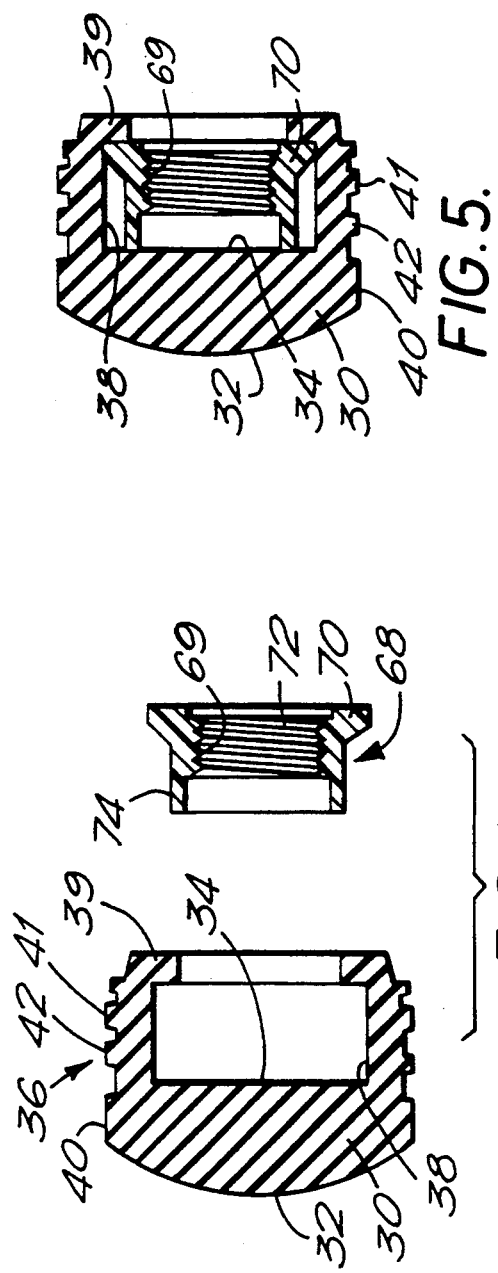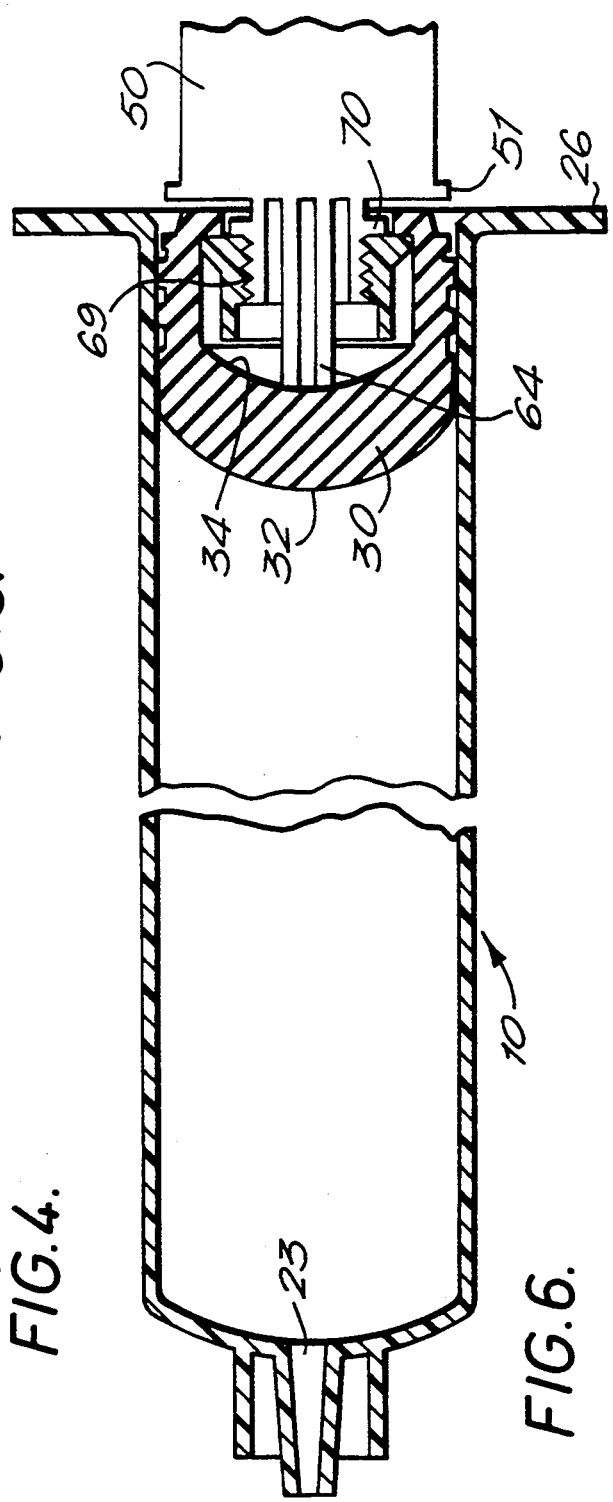

PRE-FILLED SYRINGE HAVING A PLUNGER, PLUNGER INSERT AND PLUNGER ROD

BACKGROUND OF THE INVENTION

1. Field of the Invention

This invention relates generally to pre-filled syringes for administering various fluids into a patient, more particularly, the invention relates to plastic syringes for injecting liquid pharmaceutical/biological agents, such as diagnostic imaging agents, into a patient.

2. Reported Developments

Various syringes for taking body fluid samples or administering fluid medicaments to a patient are known. Such syringes generally include a cylindrical syringe barrel, a hypodermic needle engaged with the syringe barrel, and a plunger within the syringe barrel which, when a force is exerted axially by an operator, create a suction force drawing body fluids into the barrel, or delivers fluid medicament through the hypodermic needle. The purpose of the plunger is to provide an air tight seal between itself and the syringe barrel so that movement of the plunger up and down the barrel will allow liquid, blood or other fluids to be drawn into or forced out of the syringe through the distal end.

Syringes used for such purposes include glass syringes, in which the cylindrical barrel is made of glass and the plunger is a ground glass rod which closely fits within the cylindrical barrel. In order to eliminate leakage and at the same time reduce resistance to an acceptable level, close tolerances are necessary between the barrel and the plunger along with the use of a lubricant. These glass syringes suffer from a number of disadvantages including that: they are expensive since they require close tolerances; they cannot be easily mass produced since the plungers often cannot be interchanged with one another and have to be individually fit with the barrel during the grinding process by the manufacturer; and they are susceptible to breakage.

To obviate these problems syringes were proposed and/or made by using glass and plastic barrels with plastic or elastomeric plungers. In order to prevent leakage around the plunger, the plunger is made with one or more ribs which are slightly larger in diameter in the uncompressed state than the inside of the barrel which upon placement within the barrel are compressed and deformed against the wall of the barrel and thereby form a seal. The quality and strength of the seal depend on the elastomeric properties of the material used to make the plunger and the ratio of the respective diameters of the plunger and the inside of the barrel. To obtain a good leak-proof seal, a relatively large compressive force must be exerted on the elastomeric plunger by the syringe barrel. This quality of seal, however, makes the movement of the plunger within the barrel difficult requiring excessive force on the part of the operator to move the plunger. This drawback is even more pronounced with pre-filled syringes which are maintained, ready to use, in storage. During this shelf-life the plunger tends to seize in the barrel. To remedy the problem the prior art used lubricants to reduce friction and drag between the plunger and the inside of the syringe barrel. One of the commonly used lubricants for this purpose is silicone oil. The use of such lubricants is, however, undesirable, since the lubricants tend to disperse and/or dissolve in parenteral formulations thereby contaminating the formulations. Such potential adulteration is, of course, undesirable and attempts were made to avoid the use of lubricants and still provide a leakage-proof syringe with easily slideable plunger. Such attempts included the use of various plunger configurations including one or more ribs thereon projecting forwardly or rearwardly in the barrel to reduce the frictional drag between the plunger and the barrel. Another approach was, for example in U.S. Pat. No. 5,009,646, to laminate the elastomeric plunger with a film of tetrafluoroethylene, ethylenetetrafluoroethylene and ultrahigh molecular weight polyethylene resin.

While liquid tightness and sliding property have somewhat improved with these attempts as regards to syringes intended for taking body fluid samples or injecting medicaments from stored vials, the problem of inadequate sliding property in pre-filled syringes stored for extended time periods still remain unsolved.

It is a main object of the present invention to provide a pre-filled syringe and a pre-filled cartridge which will overcome the above-described inadequate sliding property while maintaining a tight, leak-proof seal between the plunger and the wall of the syringe barrel.

It is another object of the present invention to provide a self-aspirating syringe and cartridge.

In medical practice, hypodermic injections are sometimes administered subcutaneously, while others must be given intravenously, depending upon the particular medication to be administered. In either case, it is essential that the practitioner know with certainty, prior to injection of the medication whether the hypodermic needle tip is located in a major blood vessel, such as a vein, or in subcutaneous tissue. Use of an aspirating syringe in which a negative pressure can be generated in the syringe affords a means of making such determination. Thus the appearance of blood in the syringe upon generation of the negative pressure would indicate location of the needle tip in a major blood vessel, while the lack of appearance of blood would indicate location of the tip in subcutaneous tissue. Depending upon the type of injection intended, the injection can then either proceed directly or if appropriate, the tip can be withdrawn and relocated.

Aspirating syringes are generally of two types, namely, they are either manually or automatically aspirated. In the manually aspirated type the plunger is retracted for a short distance within the barrel of the syringe. This retraction lowers the pressure within the syringe which leaves fluids at the needle tip which are then observable within the barrel of the syringe. From solid tissues no fluids will be drawn into the barrel. In the manually aspirated syringes the injection necessitates the use of both hands, one to hold the barrel, and the other to exert pressure in a rearward direction on the plunger. Such manually actuatable aspirating syringes have the disadvantage that their proper use depends on very large measure on the degree of skill of the person administering the injections.

Aspiration in syringes of the automatic or self-aspirating type is effected by first inducing a positive pressure in a medicament-containing portion of the syringe. On release of the force inducing the positive pressure, a corresponding negative pressure in the syringe is generated thus giving rise to the aspirating effect. The present invention relates to the self-aspirating type syringes.

Ideally a self-aspirating hypodermic syringe should be: relatively simple in construction so as to minimize the cost of production; should be relatively simple to operate; should be capable of manipulation with one hand; should be adaptable to multiple self-aspirating actions; should be capable of expelling trapped air from the ampoule prior to insertion of the needle into the injection site and prior to initiation of the self-aspirating action without either precluding self-aspirating action at a later time in the operation sequence of the syringe or otherwise rendering it inoperative.

The self-aspirating syringes provided by the present invention mimic, automatically, the slight rearward piston displacement withdrawal action of manually operable syringes, thus generating the slight negative pressure in the syringes essential for aspiration. The syringes of the present invention therefore obviate the disadvantage inherent in prior art syringes of the manual type, since the aspirating action is generated automatically which requires no special skill on the part of the practitioner.

These and other desirable objects will be explained as the description proceeds.

The invention will be described in reference to a pre-filled syringe; however, it is to be understood that a pre-filled cartridge, having essentially the same shape and other characteristics as a pre-filled syringe, is also intended to be described and covered by the appended claims.

SUMMARY OF THE INVENTION

The present invention comprises a syringe which is designed to be pre-filled and stored ready for injection. The syringe comprises:

(a) a barrel having an inner surface defining a cylindrical chamber for retaining an injectable fluid therein; a distal end terminating in a tapered tip to which an injection needle can be attached; and a proximal end for receiving a plunger;

(b) a cup-shaped plunger slideably mounted in said barrel and positioned close to the proximal end of the barrel to provide a seal with the inner surface of the barrel, said plunger comprising:

(1) a distal convex face which is to interface with the injectable fluid contained in the barrel;

(2) a proximal face;

(3) an outside wall contiguous with the distal convex face having thereon: distal ring, proximal ring and center ring extending radially outwardly and forming a slideable seal with the inner surface of the barrel;

(4) an inside wall;

(5) a bottom rim which together with the inside wall defines a cavity to receive a plunger insert;

(c) a rigid plunger insert having distal end and proximal end positioned within said cavity comprising: an inside wall having female threads thereon to receive and engage male threads on a plunger rod; a flange located at the proximal end having a diameter larger than the diameter of the bottom rim of the plunger so that said plunger insert is securely held within said cavity; and (d) a plunger rod having distal and proximal ends, for engaging the plunger comprising:

(1) a shoulder portion at the distal end of the plunger rod to contact bottom rim of the plunger when plunger rod is inserted in the plunger to limit elongation of the plunger;

(2) a neck portion, contiguous with the plunger rod tip, having male threads thereon to engage female threads of plunger insert; and (3) a plunger rod tip, located at the distal end of the plunger rod projecting in the direction of the plunger, the diameter of which is substantially smaller than the diameter of the plunger, and is designed to contact the proximal inside face of the plunger at the center portion thereof.

BRIEF DESCRIPTION OF THE DRAWINGS

FIG. 4 is an exploded cross-sectional view of the plunger and plunger insert taken along the line 2—2 of FIG. 1;

FIG. 5 is a cross-sectional view of the plunger and plunger insert taken along the line 2—2 of FIG. 1; and FIG. 6 is a fragmentary cross-sectional view of the syringe, plunger, plunger insert and plunger rod taken along the line 2—2 of FIG. 1.

| LIST OF REFERENCE NUMBERS USED | |
| --- | --- |
| Syringe (generally designated) | 10 |
| Barrel | 20 |
| Inside wall of barrel | 21 |
| Tapered tip of barrel at distal end | 22 |
| Bore through tip of barrel | 23 |
| Proximal end of barrel | 24 |
| Finger hub of barrel | 26 |
| Plunger | 30 |
| Convex face of plunger | 32 |
| Inside face of plunger | 34 |
| Outside wall of plunger | 36 |
| Inside wall of plunger | 38 |
| Bottom rim of plunger | 39 |
| Distal ring (on outside wall of plunger) | 40 |
| Proximal ring (on outside wall of plunger) | 41 |
| Center ring (on outside wall of plunger) | 42 |
| Plunger rod | 50 |
| Shoulder of plunger rod | 51 |
| Distal end of plunger rod | 52 |
| Proximal end of plunger rod | 60 |
| Handle of plunger rod | 62 |
| Plunger rod tip or protrusion | 64 |
| Neck portion of plunger rod | 66 |
| Plunger insert | 68 |
| Female threads on side of plunger insert | 69 |
| Flange of plunger insert | 70 |
| Male threads (on neck portion of plunger rod) | 71 |
| Inside wall of plunger insert | 72 |
| Outside wall of plunger insert | 74 |
| Flange on neck portion of plunger rod | 76 |

DESCRIPTION OF THE PREFERRED EMBODIMENTS

Figure 1:
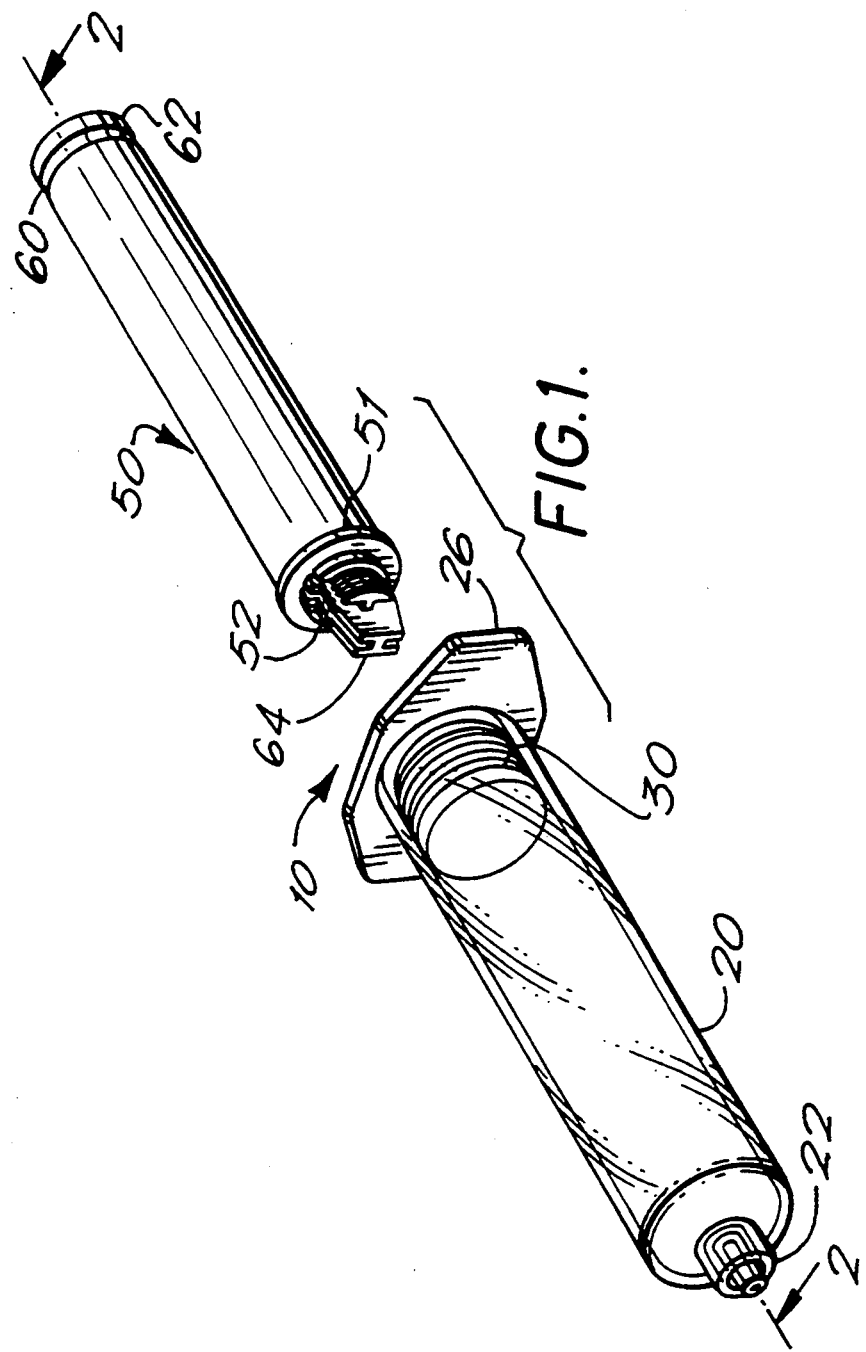
FIG. 1 is an exploded perspective view of the syringe containing a plunger and plunger insert, with plunger rod removed, according to the present invention.

Referring to FIG. 1, there is shown the syringe of the present invention generally designated 10 comprising:
barrel 20;
plunger 30; and
plunger rod 50.

Figure 2:
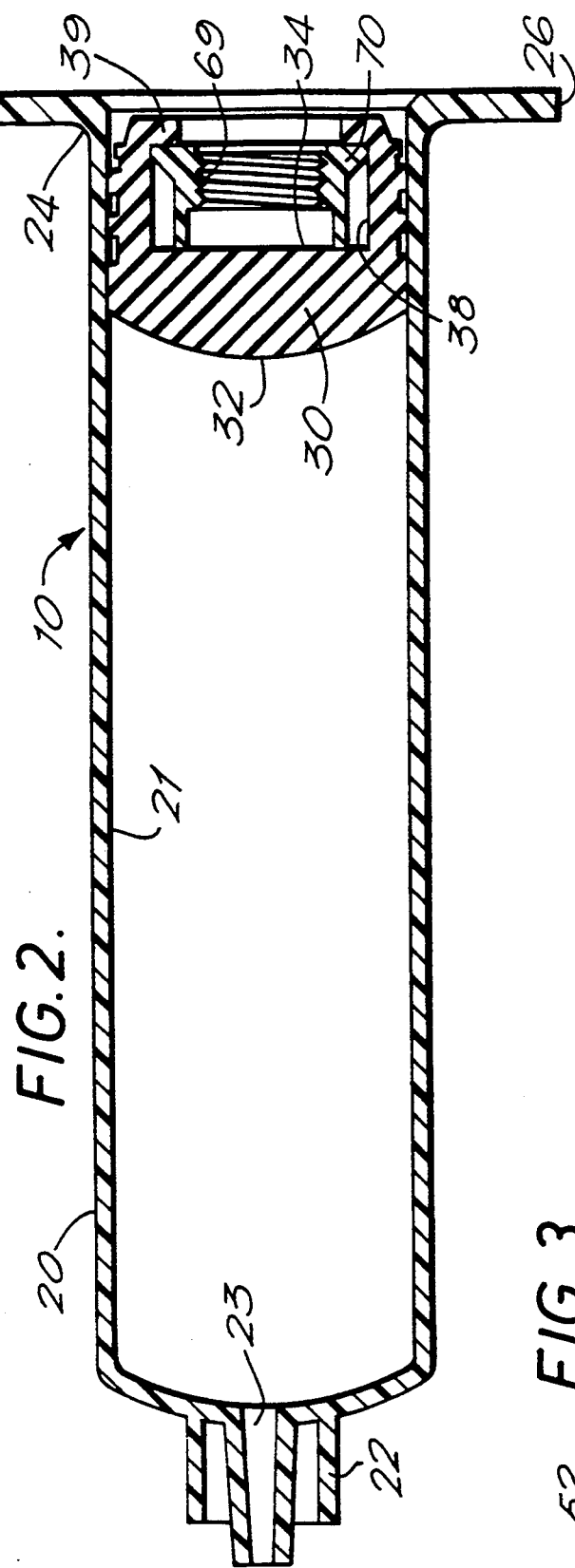
FIG. 2 is a longitudinal cross-section of the syringe and plunger taken along the line 2—2 of FIG. 1.
Figure 3:
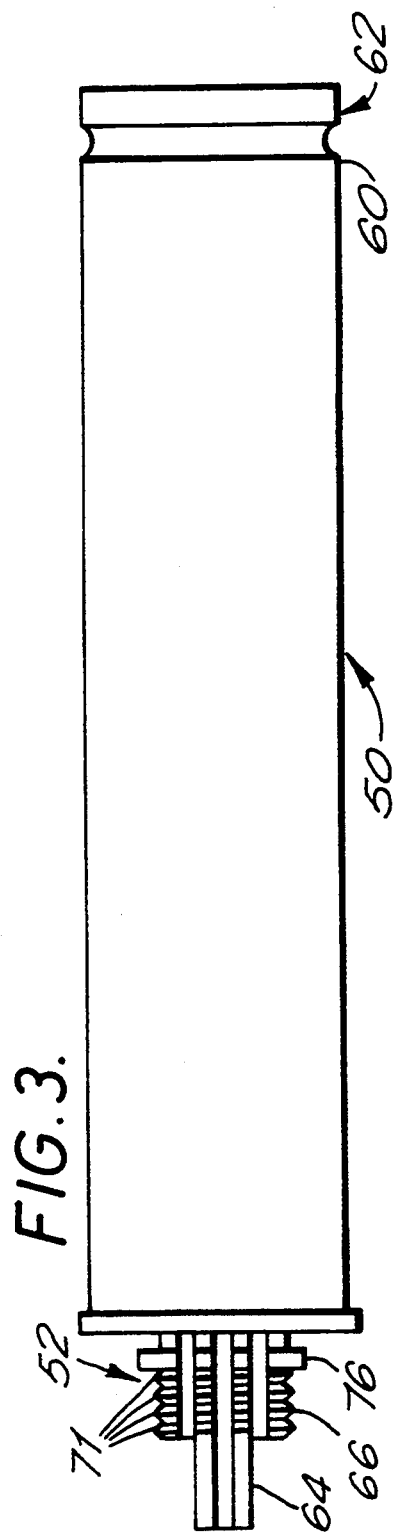
FIG. 3 is a cross-section of the plunger rod taken along the line 2—2 of FIG. 1.

Referring to FIGS. 1, 2 and 3, syringe 10 comprises: a barrel 20 having inside wall 21, a distal end terminating in a tapered tip 22 which has bore 23 therethrough, and a proximal end 24 to receive plunger 30; plunger 30 slideably positioned in barrel 20; and plunger rod 50 is attachable to plunger 30. Disposed about the periphery of proximal end 24 of barrel 20 is finger hub 26 which facilitates holding barrel 20 during operation of plunger 30 by exerting a force on plunger rod 50. Plunger rod 50, having distal end 52 and proximal end 60 comprises handle 62 to facilitate exertion of force on plunger 30 by plunger rod 50 during operation of the syringe.

Syringe barrel 20 is made of an inert gas impermeable material including glass, however, it is preferably made of a substantially transparent material that is somewhat more flexible than glass, such as polyethylene, polypropylene, polystyrenes, acrylic and methacrylic polymers.

Plunger 30 is made of a compressible, elastomeric material, such as polyisoprene rubber. Plunger rod 50 is made essentially of the same material as the barrel.

Referring to FIGS. 1, 2, 3, 4 and 6, plunger 30 is slideably received in barrel 20 and is moved axially in the barrel by a manual force exerted on plunger rod 50 which is engageable with plunger 30. Plunger 30 in its relaxed state resembles an inverted cup having: a distal convex outside face 32; a proximal inside face 34; outside wall 36 contiguous with distal convex outside face 32; inside wall 38 contiguous with inside face 34; and bottom rim 39 which defines the circular opening in the cup shaped plunger 30. Distal convex face 32 of plunger 30 is to interface with a fluid contained in barrel 20.

Outside wall 36 of plunger 30 comprises: distal ring 40, proximal ring 41, and center ring 42, which are elastically deformable and extend radially outwardly from outside wall 36 and have, when taken together with plunger 30, a minimal diameter slightly in excess of the largest diameter of the working section of barrel 20. The rings form a sealing but slideable engagement with inside wall 21 of barrel 20.

Inside wall 38, inside face 34, and bottom rim 39 define a three-dimensional cavity or area to receive plunger insert 68 of plunger 30.

Plunger insert 68 made of a rigid polymeric material, such as polyethylene, polypropylene, polystyrenes, acrylic and methacrylic polymers comprises: outside wall 74; inside wall 72 having thereon female thread 69 to receive, and engage with, male threads 71 of plunger rod 50; and flange 70. Plunger insert 68 is located in plunger 36 in such a way that the three-dimensional area defined by inside wall 38, inside face 34, and bottom rim 39 completely embraces plunger insert 68. However, the size of plunger insert 68 is such that it does not exert pressure on inside wall 38 so that outside wall of plunger 36 has sufficient space to extend in the lateral direction away from the inside wall of the syringe barrel. Flange 70 of plunger insert 68 has a diameter that is larger than the diameter of bottom rim 39 of plunger 30 so that plunger insert 68 cannot slip out form plunger 30.

Plunger rod 50 comprises: handle 62 located at proximal end 60 thereof to facilitate exertion of manual force thereon by an operator; distal end 52 having male threads 71 thereon designed to engage female threads 69 of plunger insert 68; shoulder 52; plunger rod tip 64 projecting in the direction of the plunger and extending axially forwardly from the threaded portion to form a protrusion. The diameter of said plunger rod tip is substantially smaller than the diameter of the plunger and is designed to contact the proximal inside face 34 at the center portion of plunger 30 upon exertion of pressure on plunger rod 50.

The operation of the pre-filled syringe of the present invention is as follows.

Plunger 30 is inserted into barrel 20 at the proximal end 24 thereof passed finger hub 26 so that barrel 20 may be placed pointing vertically upward with its distal end on a flat surface, such as a filling line, without interference from plunger 30. Barrel 20 is filled with the desired liquid, such as a medicament or a diagnostic imaging medium, through bore 23 in tapered tip 22 and capped. The liquid could be pre-sterilized in bulk and filled into the syringe barrel using aseptic technique or the pre-filled syringe may be sterilized by autoclaving or other means at this point.

The pre-filled, sterilized syringe is then packaged separately from a hypodermic needle and plunger rod to be assembled just prior to use. Preparatory for injection, the hypodermic needle is snapped onto the tapered distal end of the barrel. Plunger rod 50 is threaded into plunger insert 68 contained in the inside cavity of plunger 30 and tightened. The practitioner then gains entry into the desired mammalian site, such as a blood vessel, using conventional venipuncture technique. Female threads 69 of plunger insert 68 engage male threads 71 of plunger rod 50, and plunger rod tip 64 contacts inside face 34 of plunger 30.

This action causes plunger 30 to extend axially: plunger rod 50 forces plunger insert 68 towards the distal end of plunger 30. Plunger insert 68 is limited in its travel because it is pressed against the inside of bottom rim 39 of plunger 30. This axial extension reduces the diameter of the plunger, which reduces the force required to deliver the liquid from the syringe. Further force reduction is achieved when plunger rod tip 64 is forced towards the distal end of the syringe: the force distorts convex face 32 of plunger 30. The distortion, however, is limited when shoulder 51 of plunger rod 50 contacts bottom rim 39 of plunger 30. This contact between shoulder 51 and bottom rim 39 compresses the proximal end of the plunger and thereby limits the elongation of the plunger during activation.

When the operator exerts a relatively slight pressure on plunger rod 50 in a vertical upward direction, the following circumferential deformation of the plunger takes place as shown in FIG. 6: convex face 32 of plunger 30 is extended upward while distal ring 40, proximal ring 41 and center ring 42 are pulled inward by elastic tension forces. This circumferential deformation of the plunger expels head gas from the syringe, i.e. aspirates the syringe. Upon releasing the pressure applied on plunger rod 50, plunger 30 returns to its static position thereby creating a vacuum in barrel 20 and drawing body fluid from the patient indicating that the desired site had been entered and the injection may commence. Aspiration may also be accomplished by pulling the plunger via the plunger rod toward the proximal end of the barrel. By pulling on the plunger rod, plunger insert 68 exerts force only against bottom rim 39 of plunger 30 and bottom rim 39 becomes the leading edge of plunger 30 during this kind of aspiration. As such, the plunger is axially elongated allowing easy manual aspiration.

Upon completing the aspiration process, the operator exerts pressure on plunger rod 50. Referring to proximal ring 41, distal ring 40 and center ring 42, it is clear that the force they now exert on the inside wall 21 of barrel 20 is reduced in direct proportion to the rings circumferential deformation. As a result, the plunger moves relatively easily in the barrel allowing convenient delivery of the liquid into the injection site. This advantage of the present invention is even more pronounced when the pre-filled syringe is kept in storage for extended time periods during which time the plunger tends to seize in the barrel and the interfacial force between the plunger and the inside wall of the barrel is extremely difficult to break in the axial direction. In the syringe of the present invention the force exerted on the plunger pulls the distal, proximal and center rings inwardly and greatly reduces the interfacial force between the plunger and the inside wall of the barrel.

It will be appreciated from the foregoing description that the syringe of the instant invention possesses all the attributes of an ideal syringe for both aspiration and injection as described above. That is, the syringe is simple in construction, thus minimizing the cost of production; it is simple to operate; it is capable of manipulation with one hand; it is capable of multiple self-aspirating actions with each syringe or cartridge; and it is capable of expelling air trapped within the syringe or cartridge either prior to initiation of the self-aspirating action or at any time during the sequence of actions necessary for injection of the syringe content without, on the one hand, precluding self-aspirating action at any point in the sequence or, on the other, rendering the self-aspirating action inoperative.

Having thus described the invention and the advantages thereof, it is considered that the invention is to be broadly construed and limited only by the following claims.

What is claimed is:

1. A syringe designed to be pre-filled and stored ready for injection comprising:
   (a) a barrel having an inner surface defining a cylindrical chamber for retaining an injectable fluid therein; a distal end terminating in a tapered tip to which an injection needle can be attached; and a proximal end for receiving a plunger;
   (b) a cup-shaped plunger slideably mounted in said barrel and positioned close to the proximal end of the barrel to provide a seal with the inner surface of the barrel, said plunger comprising:
      (1) a distal convex face which is to interface with the injectable fluid contained in the barrel;
      (2) a proximal face;
      (3) an outside wall contiguous with the distal convex face having thereon: distal ring, proximal ring and center ring extending radially outwardly and forming a slideable seal with the inner surface of the barrel;
      (4) an inside wall;
      (5) a bottom rim which together with the inside wall defines a cavity to receive a plunger insert;
   (c) a rigid plunger insert having distal end and proximal end positioned within said cavity comprising: an inside wall having female threads thereon to receive and engage male threads on a plunger rod; a flange located at the proximal end having a diameter larger than the diameter of the bottom rim of the plunger so that said plunger insert is securely held within said cavity; and
   (d) a plunger rod having distal and proximal ends, for engaging the plunger comprising:
      (1) a shoulder portion at the distal end of the plunger rod to contact bottom rim of the plunger when plunger rod is inserted in the plunger to limit elongation of the plunger;
      (2) a neck portion, contiguous with the plunger rod tip, having male threads thereon to engage female threads of plunger insert; and
      (3) a plunger rod tip, located at the distal end of the plunger rod projecting in the direction of the plunger, the diameter of which is substantially smaller than the diameter of the plunger, and is designed to contact the proximal inside face of the plunger at the center portion thereof.

2. The syringe of claim 1 wherein said syringe barrel is made of an inert gas impermeable material selected from the group consisting of glass, polyethylene, polypropylene, polystyrenes, acrylic polymers and methacrylic polymers.

3. The syringe of claim 1 wherein said plunger is made of a compressible, elastomeric material.

4. The syringe of claim 1 wherein said plunger rod and plunger insert are made of a material selected from the group consisting of polyethylene, polypropylene, polystryenes, acrylic polymers and methacrylic polymers.

5. The syringe of claim 1 wherein said plunger rod further comprises a handle located at the proximal end thereof to facilitate exertion of manual force by an operator.

6. The syringe of claim 1 wherein said plunger is circumferentially deformed in the direction of the distal end of the barrel upon exertion of a manual force on the plunger rod, thereby pulling said distal ring, proximal ring and center ring inwardly from the inner surface of the barrel and reducing the radial force exerted on the inner surface of the barrel.

7. The syringe of claim 1 wherein said distal ring, proximal ring, and center ring are pulled inwardly by elastic forces when pressure is exerted on said plunger rod.

8. A method of delivering a liquid medium into a patient from a pre-filled syringe, said syringe comprising:
   (a) a barrel having an inner surface defining a cylindrical chamber for retaining an injectable fluid therein; a distal end terminating in a tapered tip to which an injection needle can be attached; and a proximal end for receiving a plunger;
   (b) a cup-shaped plunger slideably mounted in said barrel and positioned close to the proximal end of the barrel to provide a seal with the inner surface of the barrel, said plunger comprising:
      (1) a distal convex face which is to interface with the injectable fluid contained in the barrel;
      (2) a proximal face;
      (3) an outside wall contiguous with the distal convex face having thereon: distal ring, proximal ring and center ring extending radially outwardly and forming a slideable seal with the inner surface of the barrel;
      (4) an inside wall;
      (5) a bottom rim which together with the inside wall defines a cavity to receive a plunger insert;
   (c) a rigid plunger insert having distal end and proximal end positioned within said cavity comprising: an inside wall having female threads thereon to receive and engage male threads on a plunger rod; a flange located at the proximal end having a diameter larger than the diameter of the bottom rim of the plunger so that said plunger insert is securely held within said cavity; and
   (d) a plunger rod having distal and proximal ends, for engaging the plunger comprising:
      (1) a shoulder portion at the distal end of the plunger rod to contact bottom rim of the plunger when plunger rod is inserted in the plunger to limit elongation of the plunger;

(2) a neck portion, contiguous with the plunger rod tip, having male threads thereon to engage female threads of plunger insert; and (3) a plunger rod tip, located at the distal end of the plunger rod projecting in the direction of the plunger, the diameter of which is substantially smaller than the diameter of the plunger, and is designed to contact the proximal inside face of the plunger at the center portion thereof, said method comprising the steps of:

(i) engaging a hypodermic needle with the tapered tip of said barrel;

(ii) threading the plunger rod into the plunger;

(iii) gaining entry into the desired injection site on the patient;

(iv) exerting a slight pressure on the plunger rod to expel head gas from the barrel;

(v) releasing the pressure applied on the plunger rod to create vacuum in the syringe and drawing a small amount of body fluid from the patient and into the distal end of the barrel; and (vi) exerting pressure on the plunger rod to move the plunger toward the distal end of the barrel thereby delivering the liquid medium into the patient.

9. The method of claim 8 wherein said syringe barrel is made of an inert gas impermeable material selected from the group consisting of glass, polyethylene, polypropylene, polystyrenes, acrylic polymers and methacrylic polymers.

10. The method of claim 8 wherein said plunger is made of a compressible, elastomeric material.

11. The method of claim 8 wherein said plunger rod and plunger insert are made of a material selected from the group consisting of polyethylene, polypropylene, polystryenes, acrylic polymers and methacrylic polymers.

12. The method of claim 8 wherein said plunger rod further comprises a handle located at the proximal end thereof to facilitate exertion of a manual force by an operator.

13. The method of claim 8 wherein said plunger is circumferentially deformed in the direction of the distal end of the barrel upon exertion of a manual force on the plunger rod, thereby pulling said distal ring, proximal ring and center ring inwardly from the inner surface of the barrel and reducing the radial force exerted on the inner surface of the barrel.

14. The method of claim 8 wherein said distal ring, proximal ring, and center ring are pulled inwardly by elastic forces when pressure is exerted on said plunger rod.

15. The method of claim 8 wherein said liquid medium is a pharmaceutical composition.

16. The method of claim 8 wherein said liquid medium is a diagnostic composition.

17. The method of claim 16 wherein said diagnostic composition is a contrast agent.

18. The method of claim 8 wherein said liquid medium is a biological agent.

* * * * *